(12) United States Patent
Drazen et al.

(10) Patent No.: US 6,355,434 B1
(45) Date of Patent: Mar. 12, 2002

(54) 5-LIPOXYGENASE GENE POLYMORPHISMS AND THEIR USE IN CLASSIFYING PATIENTS

(75) Inventors: Jeffrey M. Drazen, Winchester; Kwang-Ho In, Brookline, both of MA (US); Koichiro Asano, Tokyo (JP); David Beier, Newton; James Grobholz, Lexington, both of MA (US)

(73) Assignee: Brigham & Women's Hospital, Boston, MA (US)

( * ) Notice: Subject to any disclaimer, the term of this patent is extended or adjusted under 35 U.S.C. 154(b) by 0 days.

(21) Appl. No.: 09/617,871

(22) Filed: Jul. 17, 2000

Related U.S. Application Data

(62) Division of application No. 08/846,020, filed on Apr. 25, 1997, now Pat. No. 6,090,547.
(60) Provisional application No. 60/016,890, filed on May 6, 1996.

(51) Int. Cl.[7] ................................................. C12Q 1/68
(52) U.S. Cl. ........................................................... 435/6
(58) Field of Search ............................................. 435/6

(56) References Cited

PUBLICATIONS

Hoshiko, et al., "Characterization of the Human 5–Lipoxygenase Gene Promoter", *Proc. Natl. Acad. Sci., USA*, 87: 9073–9077, 1990.
Israel, et al., "The Effect of Inhibition of 5–Lipoxygenase by Zileuton in Mild–to–Moderate Asthma", *Ann Intern Med.* 119: 1059–1066, 1993.
Israel, et al., "Effect of Treatment with Zileuton. a 5–Lipoxygenase Inhibitor, in Patients with Asthma", *JAMA*, 275(12): 931–936, 1996.
Khachigian, et al., "Egr–1 Induced Endothelial Gene Expression: A Common Theme in Vascular Injury", *Science*, 271: 1427–1431, 1996.
Laursen, et al., "Selective 5–Lipoxygenase Inhibition in Ulceratice Colitis", *The Lancet*, 335: 683–685, 1990.
Margolskee, D. "Clinical Experience with MK–571: A Potent and Specific LTD$_4$ Receptor Antagonist", *Annals New York Academy of Sciences*, 148–156, 1991.
Persson, et al., "Positive End–Expiratory Pressure Ventilation Elicits Increases in Endogenously Formed Nitric Oxide as Detected in Air Exhaled by Rabbits", *Anesthesiology*, 82(4): 969–974, 1995.
Samuelsson, et al., "Leukotrienes and Lipoxins: Structures, Biosynthesis, and Biological Effects", *Science*, 237: 1171–1176, 1987.
Weinblatt, et al., "Zileuton, A 5–Lipoxtgenase Inhibitor in Rheumatoid Arthritis", *J. Rheumatol*, 19: 1537–1541, 1992.

*Primary Examiner*—Terry McKelvey
(74) *Attorney, Agent, or Firm*—Brenda Herschbach Jarrell; Choate, Hall and Stewart

(57) ABSTRACT

The present invention provides identification of sequence polymorphisms in the 5-lipoxygenase gene that are present in general and asthmatic populations. The invention provides methods associated with correlating such polymorphisms with asthmatic phenotype and responsiveness to therapy. In particular, the invention demonstrates that individuals with reduced 5-lipoxygenase expression (or activity) are less responsive to treatment with 5-lipoxygenase inhibiters.

11 Claims, 8 Drawing Sheets

⇓ Type I Polymorphism

↓ Type II Polymorphism

```
                    -180       -170      -160      -150      -140
                     |          |         |         |         |
#1 ......GAGAAGTACT GCGGGGGCGG GGGCGGGGGC GGGGGCGGGG GCGGGGGCAG CCGGAC...
#2 ......GAGAAGTACT GCGG...... ......GGGC GGGGGCGGGG GCGGGGGCAG CCGGAC...
#3 ......GAGAAGTACT GCGG...... GGGCGGGGGC GGGGGCGGGG GCGGGGGCAG CCGGAC...
#4 ......TNCTNCCGGG GCGGGGGCGG GGGCGGGCSC GGGGGCGGGG GCGGGGGCAG CCGGAC...
```

SP-1 binding motifs (GGGCGG) are shown underlined alternating with shaded.

1 Normal sequence of the tandem SP1 binding motifs in the transcription factor binding region of the 5-lipoxygenase gene. Sequence numbering is from the GENBANK acession #M38191.SEQ HUMAN 5-LIPOXYGENASE GENE EXON #1-1/91
2 Sequence with the 12 base pair deletion
3 Sequence with the 6 base pair deletion
4 Sequence with the 6 base pair addition; note that sequence 5' of the insertion is poorly resolved.

FIG. 5

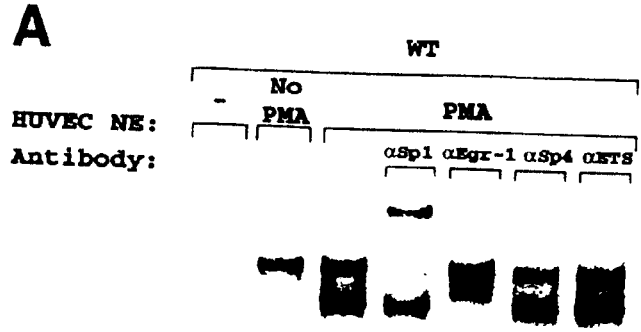
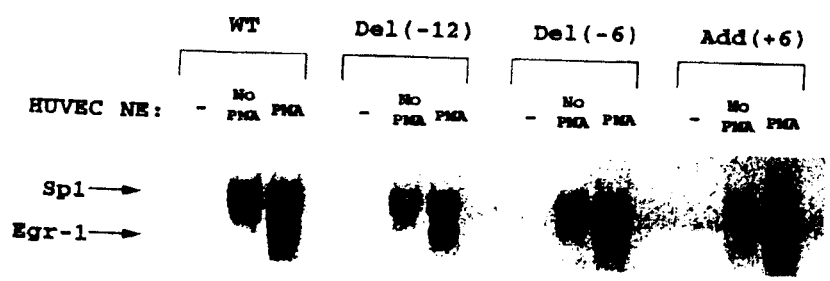
FIGURE 7

5-LIPOXYGENASE GENE POLYMORPHISMS AND THEIR USE IN CLASSIFYING PATIENTS

RELATED APPLICATIONS

The present application is a Divisional of U.S. Ser. No. 08/846,020 filed Apr. 25, 1997, issued on Jul. 18, 2000 as U.S. Pat. No. 6,090,547, which claims priority to U.S. Provisional Application Serial No. 60/016,890 filed May 6, 1996, the entire contents of both applications of which are incorporated herein by reference.

GOVERNMENT SUPPORT

Development of the present invention was supported, in part, by National Institutes of Health grant number HL-19170. The United States Government may have certain rights in the invention.

BACKGROUND OF THE INVENTION

Leukotrienes are potent pro-inflammatory mediators that are synthesized by certain bone-marrow derived granulocytes after activation (Samuelsson, *Science* 220:568, 1983; Lewis et al., *J. Clin. Invest.* 73:889, 1984). Leukotrienes have been postulated to play an important role in bronchial asthma (Margoskee, *Ann. NY Acad. Sci.* 629:148, 1990) and in other inflammatory diseases, such as ulcerative colitis, bronchitis, sinusitis, psoriasis, allergic and non-allergic rhinitis, lupus, and rheumatoid arthritis. 5-lipoxygenase is the first committed enzyme in the pathway leading to leukotriene synthesis and is responsible for the conversion of arachidonic acid to $LTA_4$ via the unstable intermediate 5-hydroperoxy eicosotetraenoic acid (Samuelsson et al., *Science* 237:1171, 1987; Samuelsson, *Science* 220:568, 1983).

It has been established that treating patients with agents that have the capacity to inhibit 5-lipoxygenase results in improvement in lung function, reduction in asthma symptoms, and decreased need for alternative asthma treatments (Persson et al., *Anesthesiology* 82:969, 1995; Israel et al., *Ann. Int. Med.* 119:1059, 1993). Treatment with 5-lipoxygenase inhibitors can also benefit ulcerative colitis patients (Laursen et al., *Lancet* 335:683, 1990) and those suffering from rheumatoid arthritis (Weinblatt et al. *J. Rheumatol.* 19:1537, 1992). However, at least in the context of asthma, not all patients experience beneficial effects; there is a heterogenous response in the patient population to treatment with 5-lipoxygenase inhibitors. Prior to the present invention, the reason for this heterogeneity was not known. Moreover, there is currently no way to identify in advance those patients who will respond well, and those who will respond poorly, to 5-lipoxygenase inhibitor treatment. Accordingly, there is a need for improvements in the area of patient response. There is also a need for further analysis of 5-lipoxygenase gene regulation.

SUMMARY OF THE INVENTION

The present invention encompasses the discovery that polymorphisms in 5-lipoxygenase gene exist within the general population and, in particular, within the asthmatic population. According to the present invention, such polymorphisms can be correlated with asthmatic phenotype (i.e., susceptibility to asthma and/or severity of disease) and/or with responsiveness to asthma therapies. The present invention therefore provides methods of asthma diagnosis and therapy. Furthermore, the teachings of this invention can readily be generalized to other inflammatory diseases that involve 5-lipoxygenase (e.g., ulcerative colitis, bronchitis, sinusitis, psoriasis, allergic and non-allergic rhinitis, lupus, rheumatoid arthritis, etc.).

Description and characterization of certain of the 5-lipoxygenase gene polymorphisms described herein reveal that different individuals have different capabilities for 5-lipoxygenase expression. Furthermore, differences in 5-lipoxygenase gene expression account for different degrees of patient responsiveness to 5-lipoxygenase inhibitors. Specifically, the present invention demonstrates that those patients who express reduced levels of 5-lipoxygenase, as compared with patients with normal 5-lipoxygenase gene expression (which patients are sometimes referred to as "normal controls"), show less responsiveness to treatment with 5-lipoxygenase inhibitors; conversely, those patients who express increased levels are more responsive to such treatment. Similar correlations can be expected for other agents that interfere with the leukotriene metabolic pathway (e.g., leukotriene receptor antagonists, 5-lipoxygenase activating protein inhibitors, etc.).

Accordingly, preferred embodiments of the present invention include methods of identifying patients who are likely to be more (or less) responsive to treatment with 5-lipoxygenase inhibitors, as compared to normal controls which methods involve identifying those patients with increased (or decreased) capability for 5-lipoxygenase expression. Analogously, the present invention provides methods defining treatments most likely to be effective for patients with altered 5-lipoxygenase gene expression and/or activity. These findings are applicable to all inflammatory diseases in which treatment with 5-lipoxygenase inhibitors (or related agents) is appropriate and, in particular, are applicable to asthma.

The present invention provides a method of classifying patients suffering from an inflammatory disease which method comprises steps of i) identifying in DNA from at least one patient a sequence polymorphism, as compared with the normal 5-lipoxygenase gene SEQ ID NO:1, in a 5-lipoxygenase gene regulatory sequence; and ii) classifying the patient based on the identified polymorphism.

The invention also provides a method of identifying an asthma patient who is a candidate for treatment with 5-lipoxygenase inhibitors, which method comprises steps of i) identifying a normal control individual who does not have asthma; and ii) identifying an asthma patient who expresses 5-lipoxygenase at a level higher than that at which the normal control expresses 5-lipoxygenase, which asthma patient is therefore identified as a candidate for treatment with 5-lipoxygenase inhibitors.

The invention further provides a method of identifying an asthma patient who is not a candidate for treatment with 5-lipoxygenase inhibitors, which method comprising steps of i) identifying a normal control individual who has normal levels of 5-lipoxygenase gene expression; and ii) identifying an asthma patient who expresses 5-lipoxygenase at a level lower than that at which the normal control expresses 5-lipoxygenase, which asthma patient is therefore identified as not being a candidate for treatment with 5-lipoxygenase inhibitors.

Additionally, the invention provides a method of identifying an individual who is susceptible to an inflammatory disorder, which method comprises steps of i) providing a nucleic acid sample from an individual; and ii) detecting in the nucleic acid sample a 5-lipoxygenase gene polymorphism that correlates with the inflammatory disorder with a P value less than or equal to 0.05, existence of the polymorphism being indicative of susceptibility to the inflammatory disorder.

The invention also provides a method of classifying an asthma patient as suffering from asthma, which method comprises steps of i) providing a nucleic acid sample from an asthmatic individual; and ii) detecting in the nucleic acid sample a 5-lipoxygenase gene polymorphism that correlates with asthma with a P value less than or equal to 0.05, existence of the polymorphism being indicative of asthma.

The invention also provides a method of treating inflammatory disorder patients which method comprises i) identifying in genetic material of one or more inflammatory disorder patients a 5-lipoxygenase gene polymorphism that correlates with increased responsiveness to a therapeutic as compared with responsiveness of an individual lacking the polymorphism; and ii) administering the therapeutic to the patient.

DESCRIPTION OF THE DRAWINGS

FIG. 5 is a schematic giving the location of polymorphisms identified in the transcription factor binding region of the 5-lipoxygenase gene (SEQ ID NO:4, (#1); SEQ ID NO:5, (#2); SEQ ID NO:6, (#3); and SEQ ID NO:7, #4). Numbering applies only to the normal sequence and is registered such that the "A" of the ATG start codon is +1.

FIGS. 7A–7B show electrophoretic mobility shift assay ("EMSA") and supershift analysis of nuclear proteins from human umbilical vein endothelial cells ("HUVEC's") HUVECs with radiolabeled oligonucleotides. Panel A shows shifts on a wild type oligonucleotide; Panel B shows shifts on mutant oligonucleotides.

DESCRIPTION OF THE SEQUENCES

Figure 1:
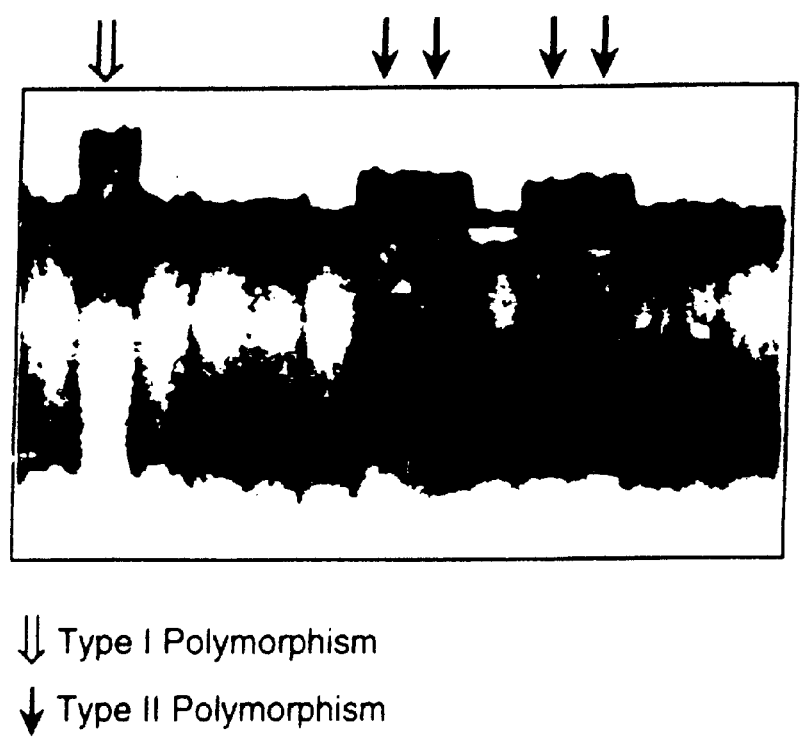
FIG. 1 is a single-stranded conformational polymorphism ("SSCP") analysis of DNA from patients with asthma. Two types of polymorphisms are noted and are indicated by arrows. The DNA from the patient marked with the double arrow was sequenced, and the sequence data are presented in FIG. 2.

SEQ ID NO:1 is the genomic 5-lipoxygenase sequence from homo sapiens (GenBank accession number M 38191). SEQ ID NO:1 includes the 5-lipoxygenase promoter and exon 1 sequence.

DESCRIPTION OF PREFERRED EMBODIMENTS

Identification of 5-Lipoxygenase Gene Polymorphisms and Mutations

The 5-lipoxygenase gene has been cloned, both as a cDNA (Matsumoto et al., Proc. Natl. Acad. Sci. USA 85:3406, 1988; Dixon et al., Proc. Natl. Acad. Sci. USA 85:416, 1988; Balcarek et al., J. Biol. Chem. 263:13937, 1988) and as a genomic clone (Hoshiko et al., Proc. Natl. Acad. Sci. USA 87:9073, 1990; Funk et al., Proc. Natl. Acad. Sci. USA 86:2587, 1989). The 5-lipoxygenase gene is approximately 85 kilobases in size and contains 14 exons and 15 introns. The region 88 to 212 base pairs upstream of the 5-lipoxygenase translation start site contains a number of sequences known to be recognition sites for transcriptional regulators (Hoshiko et al., Proc. Natl. Acad. Sci. USA 87:9073, 1990, incorporated herein by reference). For example, binding sites for AP1 and Sp1, each of which can act as either a transcriptional activator or a transcriptional repressor, depending on context, are found in this region. With respect to Sp1, there are 5 tandem binding sites (GGGCGG) found −147 to −176 base pairs upstream of the ATG translation start site. Deletion of these Sp1 sites reduces transcription from this promoter (Hoshiko et al., Proc. Natl. Acad. Sci. USA 87:9073, 1990). Sp1 sites are similarly found upstream of a variety of other genes (Li et al. Gene 164:229, 1995; Wariishi et al., Biochem. Biophys. Res. Commun. 216:729, 1995; Tang et al. Biochem. Biophys. Res. Commun. 213:673, 1995; Khachigian et al. J. Biol. Chem., 270:27679, 1995). Many of these genes have 2–3 Sp1 binding motifs; only the 5-lipoxygenase gene has five.

As described in Example 1, we have identified 5-lipoxygenase gene polymorphisms in asthmatic and non-asthmatic populations. As used herein, the term "polymorphism" means any sequence difference as compared with SEQ ID NO:1. Of particular interest are 5-lipoxygenase gene polymorphisms that represent gene mutations. As used herein, the term "mutation" means a polymorphism that has an effect on 5-lipoxygenase expression or activity. That is, a "mutant" 5-lipoxygenase gene is one that is not expressed at the same level as the gene of SEQ ID NO:1 in a particular cell, and/or that encodes a product (RNA or protein) that does not have the same activity as the corresponding product of the gene of SEQ ID NO:1.

For example, a mutant 5-lipoxygenase gene might encode an RNA that is not spliced or modified in the same way as the RNA encoded by SEQ ID NO:1. Alternatively or additionally, a mutant 5-lipoxygenase gene might encode a mutant 5-lipoxygenase protein that does not behave identically to the protein encoded by SEQ ID NO:1 in activity assays such as those described herein. Other examples of "mutant" 5-lipoxygenase genes will be readily recognized by those of ordinary skill in the art. Any 5-lipoxygenase gene that is expressed at a level that differs by at least about 20–30% from that of the wild-type 5-lipoxygenase gene (SEQ ID NO:1) under given expression conditions (i.e., in the same cell type, etc.) is considered to be a "mutant" gene according to the present invention. Also, any gene that encodes a protein whose activity level differs by at least about 20–30% from that of the wild-type 5-lipoxygenase protein (encoded by SEQ ID NO:1) is a mutant gene. Mutant gene expression (or activity) may be increased or decreased as compared with wild-type.

As described in Example 1, we have identified a variety of polymorphisms in the 5-lipoxygenase gene. Specifically, using single-stranded conformational polymorphism (SSCP), simple sequence length polymorphism (SSLP), and DNA sequencing techniques, we found polymorphisms in both the coding region and the regulatory sequences of the 5-lipoxygenase gene. Coding-region polymorphisms in the 5-lipoxygenase gene include substitutions in exon 1 (C→T at base 21), exon 2 (G→A at base 270) and exon 13 (A→G at base 1,728); regulatory sequence polymorphisms include G→A substitutions (at position −1,708 and −1,761 of the wild-type gene), a 12-base-pair deletion (of sequences corresponding to −165 to −176 of the wild-type gene), a 6-base-pair deletion (of sequences corresponding to −171 and −176 of the wild-type gene), and a 6-base-pair addition (of an Sp1 site) upstream of the gene.

Those of ordinary skill in the art will recognize that the particular methods of polymorphism identification described in Example 1 are not intended to be limiting of the present invention. Any of a variety of other known techniques, such as, for example, RNA-DNA hybrid cleavage using RNase A, mismatch detection using heteroduplex analysis, denaturing gradient gel electrophoresis, and chemical cleavage of heteroduplex DNA (see, for example, *Current Protocols in Human Genetics,* Volume 1, Chapter 7, John Wiley and Sons, 1995, incorporated herein by reference) could alternatively be used. Furthermore, these techniques can be applied to other populations, for example, to populations of patients suffering from non-asthmatic inflammatory diseases (e.g., ulcerative colitis, bronchitis, sinusitis, psoriasis, allergic and non-allergic rhinitis, lupus, or rheumatoid arthritis).

5-lipoxygenase gene polymorphisms identified as described herein are classified as "mutations" or "non-mutations" by expression and/or activity assays. Any of a variety of techniques may be employed. For example, expression of polymorphism-containing 5-lipoxygenase genes may be assayed at the RNA level using techniques, such as Northern blots, Southern blots, Differential Display, in situ hybridization, RNase protection assays, etc. (see, for example, *Current Protocols in Molecular Biology,* supra).

Alternatively or additionally, 5-lipoxygenase regulatory sequences containing polymorphisms can be analyzed, for example, by linkage to reporter genes whose activity can be measured at the RNA or DNA level, or by binding assays that test their ability to interact with relevant protein regulatory factors. Polymorphisms that contain additions, deletions, or disruptions of regulatory factor binding sites are likely to constitute 5-lipoxygenase gene mutations. A "disruption" of a regulatory factor binding site is any sequence alteration that reduces or enhances the extent to which the site is bound by the regulatory factor.

As discussed above, the 5-lipoxygenase gene contains five Sp1 sites that are involved in regulating its expression. Additional regulatory sequences can readily be identified and analyzed by promoter fusion and "promoter bashing" experiments (Orkin, *J. Biol. Chem.* 10:4955, 1995; Lederer et al., *J. Immunol.* 152:77, 1994). It is important to note that, given the propensity of eukaryotic transcriptional regulators to function at a distance (Semenza, *Hum. Mutat.* 3:180, 1994; Hill et al., *Cell* 80:199, 1995), "promoter" fragments for use in promoter fusion and "bashing" experiments should be chosen from upstream, downstream, within, and without the 5-lipoxygenase gene. At any rate, once regulatory sequences are identified in the wild-type gene, polymorphisms that disrupt the sequences can be classified as mutations.

Because binding sites for many transcriptional activators and repressors are known (Boulikas, *Crit. Rev. Eukaryot. Gene Expr.,* 4:117, 1994; Pennypacko, *Pharmacology* 51:1, 1995; Struhl, *Trends Bioch. Sci.* 14:137, 1989), those of ordinary skill in the art can readily recognize when a sequence alteration produces a new transcriptional regulator binding site. Of course, such an alteration is only likely to affect 5-lipoxygenase gene expression in the patient (and therefore to constitute a true "mutation") if the relevant transcriptional regulator is expressed in appropriate tissues (i.e., in cells of hemopoietic origin, such as mast cells, eosinophils, alveolar macrophages and related inflammatory cells). Transcriptional regulators known to be expressed in these tissues include AP1, AP3, c-fos, CK-1, CK-2, c-myc, Egr-1, GATA, GC box, NF-AT, NFκB, and TATA (see, for example, Cousins et al., *Am J. Respir. Crit. Care Med.* 150:S50, 1994; Priesch et al., *J. Immunol.* 155:4963, 1995). Thus, 5-lipoxygenase regulatory sequence polymorphisms involving additions, deletions, or disruptions of binding sites for these factors are likely to be mutations. This fact can be confirmed by expression and/or activity studies as discussed herein.

In addition (or as an alternative) to the expression techniques discussed above, 5-lipoxygenase gene mutations may be classified through analyses of the proteins they encode. For example, protein expression can be studied using immunological techniques such as Western blots, radioimmunoassays (RIA's), enzyme-linked immunoassays (ELISA's), immuno-histo-chemistry, etc. (see, for example, *Current Protocols in Molecular Biology,* Volume I and II, Ausubel et al., John Wiley and Sons, New York, 1987–96, incorporated herein by reference). Alternatively or additionally, protein activity can be tested by measuring leukotriene levels or detecting 5-lipoxygenase products (see, for example, Murphy, *J. Mass Spectrometry* 30:5, 1995; Lee et al., *Ann. Rev. Resp. Dis.* 141:1453, 1990, each of which is incorporated herein by reference).

As described in Example 1, we have identified 5-lipoxygenase gene mutations by fusing polymorphism-containing regulatory regions to a CAT reporter gene. We also tested the ability of these polymorphism-containing regulatory sequences to interact with certain protein regulatory factors. As shown, CAT activity was reduced at least about 20%, and typically at least about 50%, for each of the 6-basepair deletion, the 12-basepair deletion, and the 6-basepair insertion, as compared with a control reporter fused to the wild-type promoter (see FIG. 6). Thus, each of these polymorphisms constitutes a 5-lipoxygenase gene mutation according to the present invention.

Correlation of 5-Lipoxygenase Gene Polymorphisms and Mutations with Asthmatic Phenotype As described above, the present invention provides the discovery the 5-lipoxygenase gene polymorphisms and mutations exist within the general population. The invention further teaches that such polymorphisms and mutations can be correlated with asthmatic phenotype. Specifically, according to the present invention, polymorphisms and mutations that are found more commonly among asthmatics than non-asthmatics are diagnostic of asthmatic phenotype. Preferred diagnostic polymorphisms or mutations occur a greater proportion of the time in affected individuals (P≦0.05). Any available technique can be used to assay the 5-lipoxygenase genotype of individuals within the population (see, for example, In et al., *J. Cell Immunol.,* 1997), incorporated herein by reference). Preferred diagnostic methods of the present invention include identifying such a correlated mutation or polymorphism in the genome of an individual and, on the basis of that identification, classifying the individual as susceptible to or suffering from asthma. As used herein, an individual is "susceptible" to asthma if that person is statistically more likely to develop asthma than is a member of the general population.

In particularly preferred embodiments of the present invention, certain 5-lipoxygenase gene polymorphisms or mutations are correlated with severity and/or nature of asthmatic phenotype (e.g., with "mild", "moderate", or "severe" asthma, as defined by established clinical parameters [see, for example, Moffitt et al., *Am. Fam. Phys.*, 50:1039, 1053, 1994]; "nocturnal" or "non-nocturnal" asthma [see, for example, Busse, *Am. J. Med.*, 85:24, 1988]; etc.). For example, correlation studies as described herein are performed to identify those 5-lipoxygenase gene polymorphisms and mutations that are associated with more or less severe forms of asthma. Once identified, such polymorphisms or mutations may then be used to diagnose patients suffering from the relevant form of asthma.

Correlation of 5-Lipoxygenase Gene Polymorphisms and Mutations with Response to Therapy In particularly preferred embodiments of the present invention, 5-lipoxygenase gene polymorphisms or mutations are correlated with patient responsiveness to particular pharmacologic therapy. According to the present invention, 5-lipoxygenase gene mutations that decrease 5-lipoxygenase gene expression or activity are likely to correlate with reduced patient responsiveness to treatment with agents, such as 5-lipoxygenase inhibitors, that perform their therapeutic function by antagonizing 5-lipoxygenase. Conversely, mutations that increase 5-lipoxygenase expression are likely to correlate with increased responsiveness to such therapy. As will be understood by those in the art, agents "antagonize" 5-lipoxygenase if they reduce or interfere with its activity or expression.

The present invention demonstrates that alterations in 5-lipoxygenase gene regulatory sequences can disrupt gene expression. Insertion of new binding sites for transcriptional activators, deletion of binding sites for transcriptional repressors, or sequence substitutions that disrupt repressor binding sites or create binding sites for known activators, are likely to increase 5-lipoxygenase gene expression; conversely, sequence alterations that delete or destroy activator sites, or introduce repressor sites, are likely to decrease 5-lipoxygenase expression. In particular, deletion or addition of Sp1 and/or Egr-1 sites decreases expression at least about 20% as compared with wild-type (see Example 1). Furthermore, each of these mutations correlates with reduced responsiveness to ZYFLO™ zileuton (available from Abbott Laboratories, Abbott Park, Ill.), a 5-lipoxygenase inhibitor (see Example 2).

5-lipoxygenase gene mutations that decrease (or increase) gene expression or activity are identified as described herein. Any available technique may then be used to correlate such mutations with responsiveness to therapy. For example, as described in Example 2, a broad trial analyzing therapy effectiveness may be conducted and the data may subsequently be stratified according to 5-lipoxygenase genotype. Alternatively or additionally, the patient and control populations may first be segregated by 5-lipoxygenase genotype and then therapy effectiveness trials may be performed on each group. Any known asthma therapy may be tested in this way. For example, β-agonists, such as albuterol, may be so tested. Therapies administered for other inflammatory diseases (e.g., ulcerative colitis, bronchitis, sinusitis, psoriasis, allergic and non-allergic, rhinitis, lupus, rheumatoid arthritis, etc.) may also be so tested. New inflammatory disease therapies may also be evaluated in this way.

The present invention therefore provides methods of identifying therapies whose effectiveness varies with 5-lipoxygenase genotype, and therefore provides methods of identifying patients who are more (or less) likely to respond to a particular therapy by detecting the 5-lipoxygenase genotype in those patients. In particular, the invention provides methods of identifying patients who are less likely to be responsive to therapies whose pharmacologic action involves inhibiting or disrupting 5-lipoxygenase activity, which methods involve detecting those patients who carry 5-lipoxygenase gene mutations that reduce the gene's expression or activity level. Such patients would also presumably be more responsive to agents that increase 5-lipoxygenase activity or expression. Furthermore, such patients would also be less likely to be responsive to treatments that interfere with other aspects of the leukotriene metabolic pathway (such as, for example, leukotriene receptor antagonists, 5-lipoxygenase activating protein inhibitors, etc.).

The present invention may be illustrated by the use of the following non-limiting Examples.

EXAMPLES

Example 1

Isolation of 5-Lipoxygenase Gene Polymorphisms

Materials and Methods

PATIENT MATERIALS: Fresh whole blood was obtained from 25 patients (20 males) with asthma, according to American Thoracic Society (ATS) criteria, whose only asthma treatment was inhaled β-agonists. The forced expiratory volume in the first second ("FEV"), in these patients averaged 62.3% of predicted levels and their mean age was 39.1 yr. Fresh whole blood was also obtained form 6 patients with aspirin-sensitive asthma whose clinical characteristics had been previously detailed (Israel et al., *Am. Rev. Respir. Dis.* 148:1447, 1993) and 25 individuals (11 males) who had no history of significant medical illness, had no history of asthma or atopy, and had negative skin tests to a panel of 12 common aeroallergens. Buffy coat was separated, resuspended in RPMI, layered onto a Percoll gradient, and immortalized using Epstein-Barr virus by standard techniques (Sugden et al., *J. Virol.* 23:503, 1977; Neitzel et al., *Hum. Genet.* 73:320, 1986).

DNA was obtained by buccal brushing from an additional 81 patients with mild to severe asthma (none with aspirin-sensitive asthma by history), who received their asthma care at the Longwood Medical Area Adult Asthma Center (Boston, Mass.); these samples were used to confirm the presence of the mutations noted in the genomic DNA isolated from the immortalized cell lines noted above. In these patients the diagnosis of asthma, according to American Thoracic Society criteria, was confirmed by chart review.

POLYMORPHISM IDENTIFICATION: Genomic DNA within the 14 exons, the known positive regulatory region (854 to 931 bp upstream from the ATG start site), and negative regulatory regions (292 to 727 and 1,557 to 1,884 bp upstream from the ATG start site) was screened for polymorphisms using single-stranded conformational polymorphism (SSCP) analysis according to the method of Orita et al. (*Geronics* 5:874, 1989), with minor modifications; the oligonucleotide primers used are listed in Table I. The kinase labeling reaction was carried out by mixing 3.0 µl of [γ$^{32}$P] ATP (3,000 Ci/mmol, 10 µCi/µl), 1.7 µl of 20-µM primers each, 37.1 µl dH$_2$O, 5.0 µl of 10 X T4 polynucleotide kinase buffer, and 1.5 µl of T4 polynucleotide kinase (10 U/µl). The mixture was incubated at 37° C. for 45 min and then at 66–70° C. for 10 min. The PCR reaction volume was 12.5

μl containing 100–250 ng of genomic DNA in the presence of 1 μl of $^{32}$P-labeled primers (0.13 μM each), dNTPs (0.4 mM each), MgCl$_2$ (1.6 mM) and Taq DNA polymerase (0.5 U).

Malvern, Pa.). Electrophoresis was performed, using a DNA sequencing apparatus, at a constant temperature of 4° C. and a 40 W. After 5 to 6 hours, the gel was dried and exposed to X-ray film.

TABLE 1

PCR Primers Used in Mutation Identification and Sequencing of the 5-Lipoxygenase Gene

| Region of Interest | Sense primer (5' to 3') | Antisense primer (5' to 3') |
|---|---|---|
| Negative regulatory region* (-1,557 to -1,844) | AAAGAACAGCGTTGGTGGAT SEQ ID NO:8 | CAAATTCATTGTGTTGCATGTG SEQ ID NO:9 |
| (-292 to -727) | ACCACTGGCCATCTCTGG SEQ ID NO:10 | CTCTCAGCGAGGTGTCTG SEQ ID NO:11 |
| Positive regulatory region* (-854 to -931) | TTAGCCGAGATCAATACACGC SEQ ID NO:12 | GGGTGTGGAGAAGGTTTCG SEQ ID NO:13 |
| Transcription factor binding region* (-88 to -212) | AGGAACAGACACCTCCTGAGGAGCA SEQ ID NO:14 | GAGCAGCGAGCGGGAGCCTCGGC SEQ ID NO:15 |
| Exon 1 | CGCCATGCCCTCCTACAC SEQ ID NO:16 | CCACGCTGGAAGTCGTTGTA SEQ ID NO:17 |
| Exon 2 | TCTCCTTCCCAGGTGGAT SEQ ID NO:18 | GCTCACCGCGTCC SEQ ID NO:19 |
| Exon 3 | CTTTCTTTACAGCAAAAGTTG SEQ ID NO:20 | taxaACTCACCGATATTG SEQ ID NO:21 |
| Exon 4 | TCTCATGCTCAGATGGATG SEQ ID NO:22 | ACTTACGCTTTGGA SEQ ID NO:23 |
| Exon 5 | TGGAGAACCTGTTCATCAACC SEQ ID NO:24 | TCACCAGAAATAGTGTTGCTGA SEQ ID NO:25 |
| Exon 6 | CCTGGTAGAGCGGGTCATGAATC SEQ ID NO:26 | ACCTCCTGCTCCAAGCTGAGCT SEQ ID NO:27 |
| Exon 7 | TCGCTCCTGCAGCAAGGG SEQ ID NO:28 | GCCTACCTGGAT SEQ ID NO:29 |
| Exon 8 | CCAATGTATGAGCTCAAC SEQ ID NO:30 | getatcCTGTACCTTGAA SEQ ID NO:31 |
| Exon 9 | CCCTCCCCAGCTGCTGGT SEQ ID NO:32 | ACCCACCTTGTCAAAGCGGCC SEQ ID NO:33 |
| Exon 10 | CACTCCAGGCCAACGCCACA SEQ ID NO:34 | CCACACCAGGAGCCCCGTCGT SEQ ID NO:35 |
| Exon 11 | CCCCTGAGCCAGGTTCACG SEQ ID NO:36 | ccacgaaCCCTACCTGAGGA SEQ ID NO:37 |
| Exon 12 | TTCCACCCTAGGCTTCCC SEQ ID NO:38 | GCCTACCTGGCCCCAAGTT SEQ ID NO:39 |
| Exon 13 | GTGCTCCTGGATCCCCAAT SEQ ID NO:40 | CTCGTTTTCCTGGAACTGGC SEQ ID NO:41 |
| Exon 14 | CTGGGCCCTCAGCTGTTC SEQ ID NO:42 | CACATGGAACAAGACCCATT SEQ ID NO:43 |

*Position is reference to the ATG translation start site as +1.

Amplification of the highly G+C-rich transcription factor binding region (88 to 212 bp upstream from the ATG start site) required different PCR conditions. A reaction volume 20 μl was used containing 250 ng of genomic DNA in the presence of 2 μl of $^{32}$P-labeled primers (0.2 μM of each primer), dATP (0.2 mM), dCTP (0.2 mM), of dTTP (0.2 mM), a 3:1 ratio of dGTP to 7-deaza-dGTP (0.2 mM), 1 μl of DMSO, 2 μl of Taq extender PCR additive (Stratagene Inc., La Jolla, Calif.), and Taq polymerase (1 U). PCR was performed (PTC-100TM programmable thermocycler; MJ Research, Inc., Waltham, Mass.) for 35 cycles (each cycle was 94° C. for 1 min, 56–62° C. for 1 min, and 72° C. for 1 min).

PCR products were diluted (1:10) in a sequencing stop solution (95% formamide, 20 mM ethylenediaminetetraacetic acid ("EDTA") EDTA, 0.05% (w/v) xylene cyanol, 0.05% (w/v) bromophenol blue). Denaturation was carried out at 95° C. for 10 min and samples were immediately loaded on a nondenaturing acrylamide gel (AT Biochem, SIMPLE SEQUENCE LENGTH POLYMORPHISM (SSLP): Because sequence analysis showed polymorphisms that modified the number of Sp1 and Egr-1 binding motifs, the transcription binding region (212 to 88 bp upstream from the translation start site) of genomic DNA from a number of individuals was analyzed by SSLP (Weber et al., Am. Hum. Geret. 44:388, 1989). SSLPs were carried out either using $^{32}$P-labeled primers or including [α-$^{35}$S] dATP in the PCR reaction mix. PCR amplification reactions for the $^{32}$P-labeled primers were performed similar to the method used for SSCP. The amplification of genomic DNA that involved the inclusion of [α-$^{35}$S] dATP was carried out according to the following method. The PCR mixture in 25 μl contained 500 ng of genomic DNA, PCR buffer (Boehringer Mannheim, Mannheim, Germany), 2.5 mM MgCl$_2$, 200 μM dCTP and dTTP, 50 μM dGTP, 150 μM 7-deaza-dGTP, 10 μM dATP, 6.25 μCl of [α-$^{35}$S] dATP (Dupont-New England Nuclear, Boston, Mass.) 10 pmoles of each primer, 5% DMSO, and 1.5 U of Taq polymerase. The PCR conditions were: 6 min at 94° C., followed by 31 cycles of 94° C. for 15 s, 62° C. for 23 s, and 72° C. for 30s. Chain elongation was continued after the last cycle for 5 min. 10 µl of PCR product was mixed with 5 µl of stop solution. Samples were denatured at 95° C. for 5 min., and 6 µl of each sample was loaded on a 6% denaturing acrylamide gel; the gel was run at room temperature for 2.5 h at 60 W. Gels were dried and exposed to X-ray film as required (Maniatis et al., *Molecular Cloning, A Laboratory Manual,* Cold Spring Harbor Press, CSH, N.Y.).

DNA SEQUENCING: Direct cycl sequencing was performed on target sequences that were amplified by using the primers employed for PCR-SSCP analysis. The PCR mixture contained 2 µM of both primers, 0.2 mM of dNTP mixture, 0.5 µg of genomic DNA, reaction buffer (1X), and 1.25 units of Taq polymerase (GIBCOBRL) in a total volume of 50 µl. PCR was performed in a PCT-100TM programmable thermocycler for 30 cycles (each cycle was 95° C. for 30 s, 56–62° C. for 30 s and 72° C. for 1 min). The PCR products wee purified by PCR product purification Kit (Promega), and were used as template DNA in direct cycle sequencing reactions.

PCR primers were used as the sequencing primers. Primers were labeled using T4 polynucleotide kinase using the following reaction mixture: 1 µl primer (20 pmol/µl), 1 µl 10 X kinase reaction buffer, 4.5 µl [γ-$^{33}$P]ATP (1700 Ci/mmol, 10 mCi/µl), 2.5 µl H$_2$O, 1 µl T4 polynucleotide kinase (10 U/µl). The mixture was incubated at 37° C. for 30 min, then heated to 90° C. for 10 min to inactive the kinase.

One microliter of labeled primer was mixed with template DNA (60–80 fmol), 4.5 µl of reaction buffer (300 mM Tris-HCl, pH 9.0, 50 mM MgCl$_2$, 300 mM (KCl) and 1.25 units of Taq DNA polymerase (GIBCOBRL, Gaithersburg, Md.) in a total volume of 36 µl. Then, 8 µl of the labelling mixture was transferred to each of the 4 terminal tubes containing 2 µl of the termination mixture (A, G, C and T) as described in the dsDNA Cycle Sequencing System Kit (GIBCOBRL). PCR amplification was carried out with 20 cycles of a denaturation step of 94° C. for 30 s, an annealing step at 56° C. for 30 s, and an extension/termination step at 72° C. for 1 min, followed by 10 cycles of a denaturation step at 94° C. for 30 s and an extension/termination step at 72° C. for 1 min. The reaction was stopped with 5 ml stop solution (95% formamide, 20 mM EDTA, 0.05% bromophenol blue, and 0.05% xylene cyanol). All samples were incubated at 90° C. for 2 min and 3 µl of each sample were loaded onto an 6% sequencing gel. To sequence both alleles from heterozygous individuals, DNA from two clones (wild type and mutant) from TA cloning that showed migration differences on a 3% agarose gel were sequenced.

Automated sequencing was performed at Children's Hospital (Boston) Sequencing facility using ABI (Applied Biosystems, Inc., Foster City, Ca.) technology.

CHLORAMPHENICOL ACETYL TRANSFERASE (CAT) REPORTER ASSAYS: Plasmids 5LO-CAT were constructed using the pCRII vector (Invitrogen Corp., San Diego, Ca.) or the pCAT-Ehancer vector (Promega Corp., Madison, Wis.)) as indicated by each respective manufacturer (see In et al., *J. Clin. Invest.,* 99:5, 1997, incorporated herein by reference). PCR-amplified segments from genomic DNA isolated from individuals who harbored the various polymorphisms identified in the 5-LO gene promoter was subcloned into the pCRII (p5LOpCRII) vector. (in wild type DNA, the amplified segment was 280 bp and consisted of the 5-LO DNA 294 to 15 bp upstream from the ATG translation start site. The size of the amplified fragment differed among the various polymorphic forms of DNA.)

The 5-LO upstream region was isolated from p5LPpCRII by restriction enzyme digestion with HindIII and XbaI and ligated into the pCAT-Enhancer vector to generate p5LO-CAT. HeLa cells were cultured in 60-mm diam culture dishes in modified Eagle's medium supplemented with 10% (vol/vol) fetal calf serum ("FCS"). p5LO-CAT was transfected into these cells when they reached 50–70% confluence using transfection (Promega Corp.). Cells were harvested 48 h after transfection, lysed and lysates analyzed for CAT activity by standard techniques (Finn et al., *Proc. Natl. Acad. Sci. USA* 87:914, 1990; Ausubel et al., *Current Protocols in Molecular Biology* John Urley & Sons, N.Y., 1993). The transfections were internally controlled by cotransfection with the plasmid vector pXGH5 containing the human growth hormone (HGH) structural sequence (Nichols Institute, San Juan Capistrano, Calif.). Human growth hormone activity of the cell supernatant was used to normalize the CAT results from transfection efficiency using the HGH-TGES 100% kit (Nichols Institute) according to the manufacture's instructions.

OLIGONUCLEOTIDE SYNTHESIS, PURIFICATION, AND RADIOLABELING: Oligonucleotides for supershift analysis and electrophoretic mobility shift assay (EMSA) using recombinant proteins were synthesized on a 392 DNA/RNA Synthesizer (Applied Biosystems, Inc.). Complementary strands were annealed, purified by nondenaturing polyacrylamide gel electrophoresis, and end-radiolabeled with [γ-$^{32}$P] ATP (DuPont-NEN, Boston, Mass.) using T4 polynucleotide Kinase (New England BioLabs Inc., Beverly, Mass.).

NUCLEAR EXTRACT PREPARATION: Compartmental extracts from HUVEC's grown in tissue culture were prepared by a modification of the method of Dignam et al. (*Nuc. Acids Reg.*11:1475, 183). At confluence, monolayers were washed twice with PBS at 4° C. and collected, using a rubber policeman, in a 50-ml conical tube on ice. Cells wee pelleted and lysed, and the nucleic were pelleted; the nuclei were then resuspended, lysed, vortexed, and centrifuged (Khachigian et al., *Science* 271:1427, 1996). Supernatants containing nuclear proteins were removed, immediately frozen on dry ice, and stored at −80° C.

RECOMBINANT PROTEINS: Recombinant Egr-1 (zinc finger region) was generously provided by Dr. F. J. Raucher III (Wister Institute of Anatomy and Biology, University of Pennsylvania, Philadelphia, Pa.). Samples were stored at −80° C. in dilutions of 1:10, 1:50, 1:200, and 1:500 containing 25 mM Hepes-KOH, pH 7.5, 100 mM KCl, 10 mM ZnSo$_4$, 0.1% Nonidet P-40, 1 mM DDT, and 50% glycerol. Recombinant Sp1 (Promega Corp.,), purified from HeLa cells infected with recombinant vaccinia virus containing human Sp1 cDNA, was stored similarly in 12 mM Hepes-KOH, pH 7.5, 50 mM KCl, 6 mM MgCl$_2$, 5 mM ZnSO$_4$, 0.05% Nonidet P-40, 1 mM DTT, and 50% glycerol.

ELECTROPHORETIC MOBILITY SHIFT ASSAY (EMSA) AND SUPERSHIFT ANALYSIS: In vitro binding reactions between oligonucleotides and nuclear extract were done in a total volume of 20 µl containing: 2 µL of 10 X binding buffer (0.1 M Tris-HCl, pH 7.5, 50% glycerol, 10 mM EDTA, 10 mM dithiothreitol), 1 µl of 1 mg/ml poly (dI,dC) (Sigma Chemical Co.), 1 µl of 1 mg salmon sperm DA (Sigma Chemical Co.), 3 µl of nuclear extract (normalized to ~8 mg/ml to total protein), and 1 µl radiolabeled oligonucleotide (specific activity 50,000 cpm/reaction). Binding reactions involving recombinant proteins contained 2 µl of the appropriate dilution and 1 µl of mg/ml BSA as a protein carrier. The reaction was allowed to proceed for 30 min at 22° C. before the addition of nondenaturing loading buffer (0.2% bromophenol blue, 0.2% xylene cyanol, 20% glycerol). Samples were electrophoresed for ~1.5 h. Gels were dried under vacuum and autoradiographed overnight. Supershift studies were performed as above except 1 μl (1 μg) of the appropriate antibody (Santa Cruz Biotechnology, Inc., Santa Cruz, Ca.) was added 10 min before the addition of radiolabeled oligonucleotide. When appropriate, densitometric analysis was completed on the autoradiographs using ImageQuant software (Molecular Dynamics, Sunnyvale, Calif.).

STATISTICS: CAT activity relative to HGH transcription of the various constructs was compared by analysis of variants ("ANOVA"); when significant differences were noted among groups, they were compared by Student's t test. Differences in allele frequency among groups were calculated using Fisher's exact test.

Results

CODING REGION POLYMORPHISMS: Polymorphisms consisting of a change in a single base pair were identified in exon 1 (C→T at base 21), exon 2 (G→A at base 270), and exon 13 (A→G at base 1,728). At the locus identified in exon 1, there were 6 heterozygotes among the 25 nonaspirin-sensitive asthmatic subjects, 3 among the 6 aspirin-sensitive asthmatic subjects, and 5 among the 25 normal subjects; allele frequencies are given in Table II.

TABLE II

Allele Frequencies at 5-LO Gene Polymorphisms

| | | Allele frequency | | |
| --- | --- | --- | --- | --- |
| | | Asthmatic | | |
| Locus | Allele type | Nonaspirin-sensitive | Aspirin-sensitive | Normal |
| Negative regulatory region (−1557 to 1,844) | Wild-type | 0.88 (44/50) | 0.83 (10/12) | 0.80 (40/50) |
| | G1708→A G1761→A | 0.12 (6/50) | 0.17 (2/12) | 0.20 (10/50) |
| Transcription factor binding region | Wild type | 0.78 (165/212) | 0.75 (9/12) | 0.76 (38/50) |
| | 12-bp deletion* | 0.06 (12/212) | 0.00 (0/12) | 0.02 (1/50) |
| | 6-bp deletion* | 0.14 (30/212) | 0.25 (3/12) | 0.18 (9/50) |
| | 6-bp addition* | 0.02 (5/212) | 0.00 (0/12) | 0.40 (2/50) |
| Exon 1 | Wild type | 0.88 (44/50) | 0.75 (9/12) | 0.90 (45/50) |
| | C21→T | 0.12 (6/50) | 0.25 (3/12) | 0.10 (5/50) |
| Exon 2 | Wild type | 0.94 (47/50) | 1.00 (12/12) | 1.00 (50/50) |
| | G270→A | 0.06 (3/50) | 0.00 (0/12) | 0.00 (0/50) |
| Exon 13 | Wild type | 0.92 (46/50) | 1.00 (12/12) | 0.94 (47/50) |
| | A1728→A | 0.08 (4/50) | 0.00 (0/12) | 0.06 (3/50) |

Allele frequencies in the nonaspirin-sensitive asthmatic subjects are given for the 25 patients with immortalized DNA and the 81 patients from whom check brushings were available.
*Location of the additions/deletions identified in the text.

At the locus identified in exon 2, there was one heterozygate and one homozygote among the 25 nonaspirin-sensitive asthmatic subjects; this polymorphism was not found in the 6 aspirin-sensitive asthmatic or the 25 normal subjects. A the locus identified in exon 13, there were 4 heterozygotes among the 25 nonaspirin-sensitive asthmatic subjects, no heterozygotes among the 25 nonaspirin-sensitive asthmatic subjects, no heterozygotes among the 6 aspirin-sensitive asthmatic subjects, and 1 heterozygote and 1 homozygote among the 25 normal subjects. Each of these polymorphisms represents a conservative substitution in that the amino acid sequence of the putative 5-LO protein derived from the polymorphic DNA would not be changed. In the sample of DNAs examined, there was no significant difference in the allele frequency of each of these polymorphisms between the normal and asthmatic subjects. Among the 25 normal and 31 asthmatic individuals examined, there were no polymorphisms noted by SSCP in exons 3–12 and 14.

POLYMORPHISMS IN THE 5' FLANKING REGION: Polymorphisms, consisting of a change in a single base pair, were noted in the negative regulatory region (as defined by Hoshiko et al. [*Porc. Natl. Acad. Sci. USA*, 86:2587, 1989] between positions 1,844 and 1,557 upstream form the ATG translation start site; these consisted of a G→A substitution at −1,708 and a G→A substitution at −1,761. All subjects with the G→A substitution at −1,708 also had the G→A substitution at −1,761. There were six nonaspirin-sensitive asthmatics (heterozygotes), two aspirin-sensitive asthmatics (heterozygotes), and nine (eight heterozygotes and one homozygote) normal subjects with these mutations.

A family of polymorphisms was noted in the transcription factor binding region 212 to 88 bp upstream from the translation start site. The first member of this family was originally termed a "type I" polymorphism by SSCP as defined in FIG. 1. This polymorphic allele was present in two samples (one homozygote and one heterozygote) of immortalized lymphocyte DNA from non-aspirin-sensitive asthmatic subjects and one normal subject (heterozygote); it was not identified in any aspirin-sensitive asthmatic subjects. Direct cycle sequencing of the DNA obtained from the individual homozygous for this polymorphic allele, FIG. 2, indicated the presence of a 12-bp deletion, -GGGCGGGGGCGG-(or -(GGGCGG)$_2$-), from the wild-type sequence between positions -165 and 176 (1669–1680 of SEQ ID NO:1). Interestingly, this deletion consisted of two of the known five tandem repeats of the consensus Sp1 binding sequence (Karin et al., *Nature* 308:513, 1984; Ishii et al., *Science* 232:1410, 1986; Harrington et al., *Proc. Natl. Acad. Sci. USA* 85:2066, 1988), which are present between 147 and 176 bp upstream from the ATG start site of the 5-LO gene.

Figure 2:
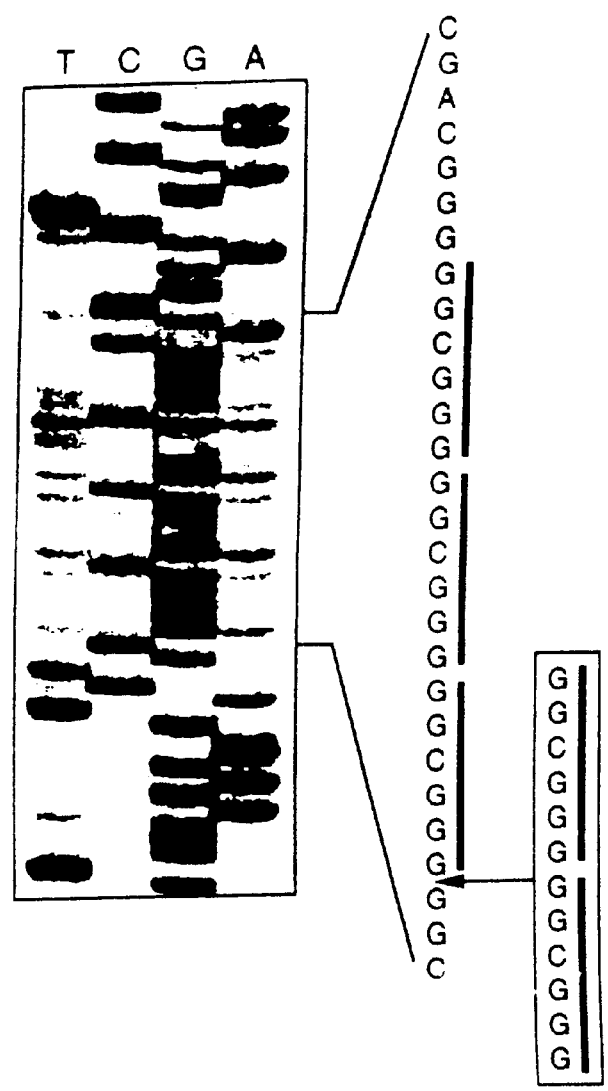
FIG. 2 presents direct cycle sequencing data of the 5-lipoxygenase gene promoter region from the patient marked with the double arrow in FIG. 1. The column to the right gives the sequence read from the autoradiograph (SEQ ID NO:2), while the box to the far right indicates the area of missing sequence (SEQ ID NO:3).
Figure 3:
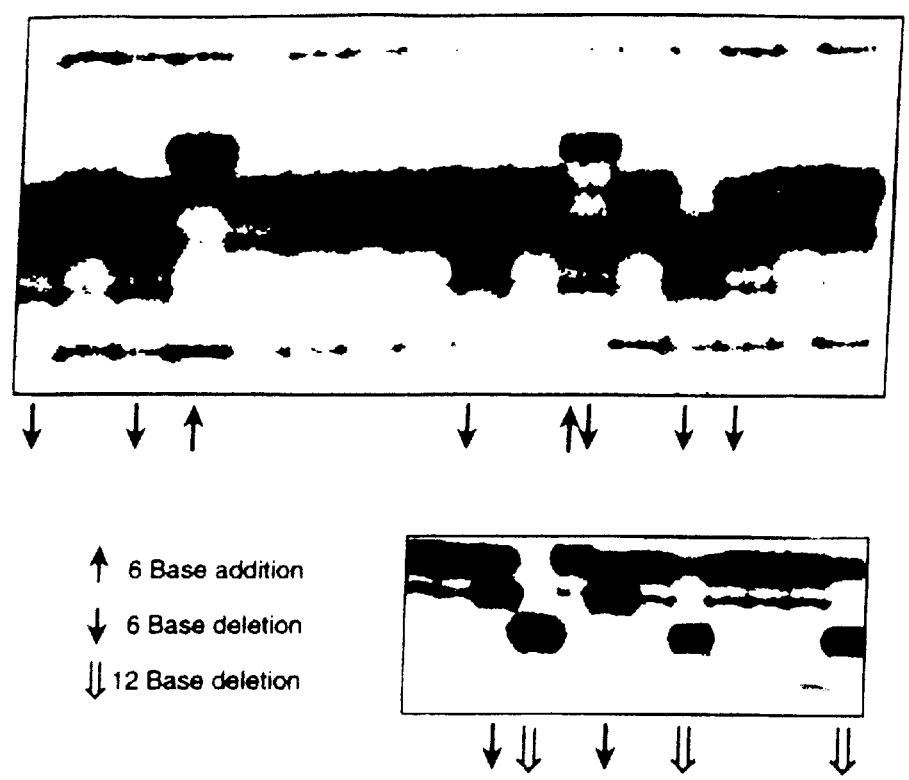
FIG. 3 is a simple sequence length polymorphism ("SSCP") analysis of DNA from patients with asthma, and shows the mobility of fragments with the wild type sequence, with the 6 base pair addition, with the 6 base pair deletion, and with the 12 base pair deletion.
Figure 4:
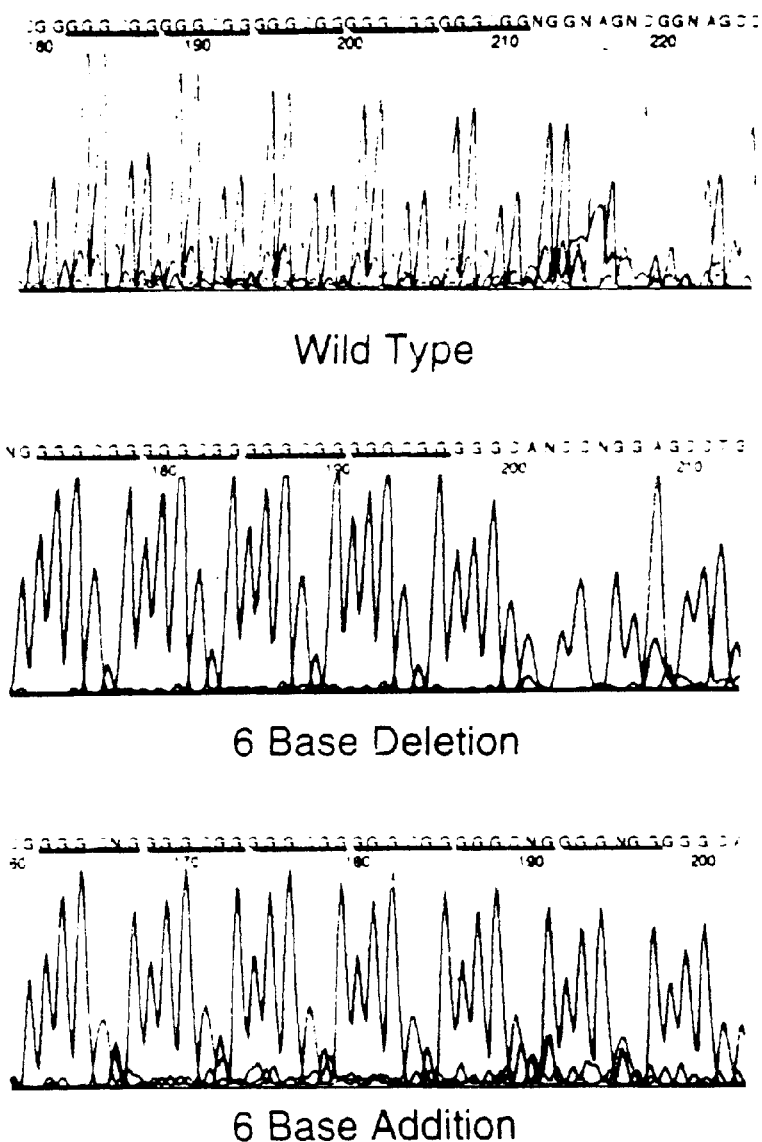
FIG. 4 presents automated sequencing analysis of DNA from a normal individual and from two asthmatic patients with polymorphisms in 5-lipoxygenase gene regulatory sequences.

The DNA from individuals harboring the "type II" polymorphisms in FIG. 1 was resolved using automated sequencing as a 6-bp deletion consisting of a loss of a single Sp1 and Egr-1 binding motif between positions −171 and −176. Because these polymorphisms, i.e., a deletion of one and two Sp1 or Egr-1 binding motifs, substantially modified the length of the DNA fragments obtained by PCR, we screened genomic DNA from an additional 81 asthmatics using SSLP. This led to the identification of a third polymorphic form of DNA, FIG. 3, identified by automated sequencing as a 6bp addition of a Sp1 binding domain. The polymorphic alleles identified at this locus are compared to the wild-type sequence in FIG. 5. Among the 61 individuals from whom immortalized DNA was available, there were 23 individuals harboring polymorphic alleles as indicated by SSLP. In 14 of these individuals, the inferred polymorphism was configured by automated sequencing (data not shown).

HAPLOTYPIC REFERENCES: When DNA sequences from the wild type and polymorphic DNA sequences were compared, it was determined that individuals heterozygous or homozygous for the 12-bp deletion were also heterozygous or homozygous for the polymorphism noted in exon 2, respectively. Similarly, we determined that individuals heterozygous or homozygous for the 6-bp deletion were also heterozygous for the polymorphism noted in exon 1. These findings are consistent with the presence of a haplotype in which the 6- and 12-bp transcription factor binding region polymorphisms are in linkage disequilibrium with the previously noted exon 1 and exon 2 polymorphisms, respectively.

Figure 6:
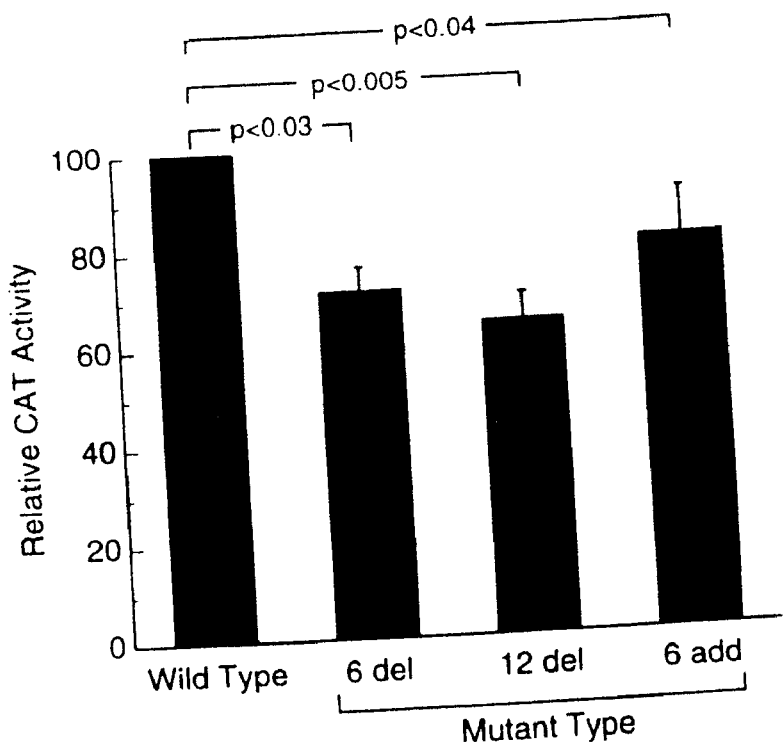
FIG. 6 shows the relative CAT activity, corrected for transfection efficiency, of reporter constructs in which either wild-type or polymorphism-bearing 5-lipoxygenase sequences are linked to the CAT gene. Results are the mean of five experiments, each of which was performed in triplicate.

CAT REPORTER ASSAYS: To determine whether functional differences existed among the various forms of the 5-LO transcription factor binding region that we had identified, we constructed a panel of CAT reporter gene constructs containing the wild type, the 12-bp deletion, the 6-bp deletion or the 6-bp addition. The CAT activity in relationship to the activity of the co-reporter plasmid pHGH is shown in FIG. 6; data shown are the man of 5 separate transfections, each performed in triplicate. The relative CAT activity of the constructs containing the 12-bp deletion, the 6-bp deletion, or the 6-bp addition was significantly less than the CAT activity of the wild type constructs, P=0.0047, P=0.022, and P=0.038, respectively. Each of these polymorphisms therefore constitutes a 5-LO gene mutation.

EMSA: To further characterize the wild type and mutant forms of the 5-LO transcription factor binding region, EMSA's were used to detect specific DAN-nuclear protein interactions. The ubiquitous transcription factor SPl is known to bind the functionally important G+C-rich region of the 5-LO promoter (Hoshiko et al., *Proc. Natl. Acad. Sci. USA* 87:9073, 1990). The inducible transcription factor Egr-1 shares a similar G+C-rich consensus binding motif with Sp1, and Sp1/Egr-1 interactions may be important in the transcriptional regulation of many genes (Khachigian et al., *Science* 271:1427, 1966), We therefore proposed that Egr-1 would also be capable of interacting with the 5-LO G+C rich sequence as well as Sp1. Moreover, we hypothesized that Sp1 and Egr-1 binding difference may be partially responsible for the functional differences detected with our CAT reporter assays.

Because HUVEC are known to produce Sp1 and phorbol-myristate-acetate-(PMA)-inducible Egr-1, they were used as a source of nuclear extracts. EMSA with unstimulated HUVEC nuclear extract produced a single intense band (FIG. 7). Nuclear extract prebound to anti-Sp1 antibodies supershifted the upper band, whereas anti-Egr-1 antibodies supershifted the lower band. Identical concentrations of antibodies to Sp1 and ETS (a nuclear binding protein with transactivating properties) factors produced no change. These data suggest that Sp1 and inducible Egr-1 are capable of binding the wild type G+C rich region of 5-LO.

Figure 8:
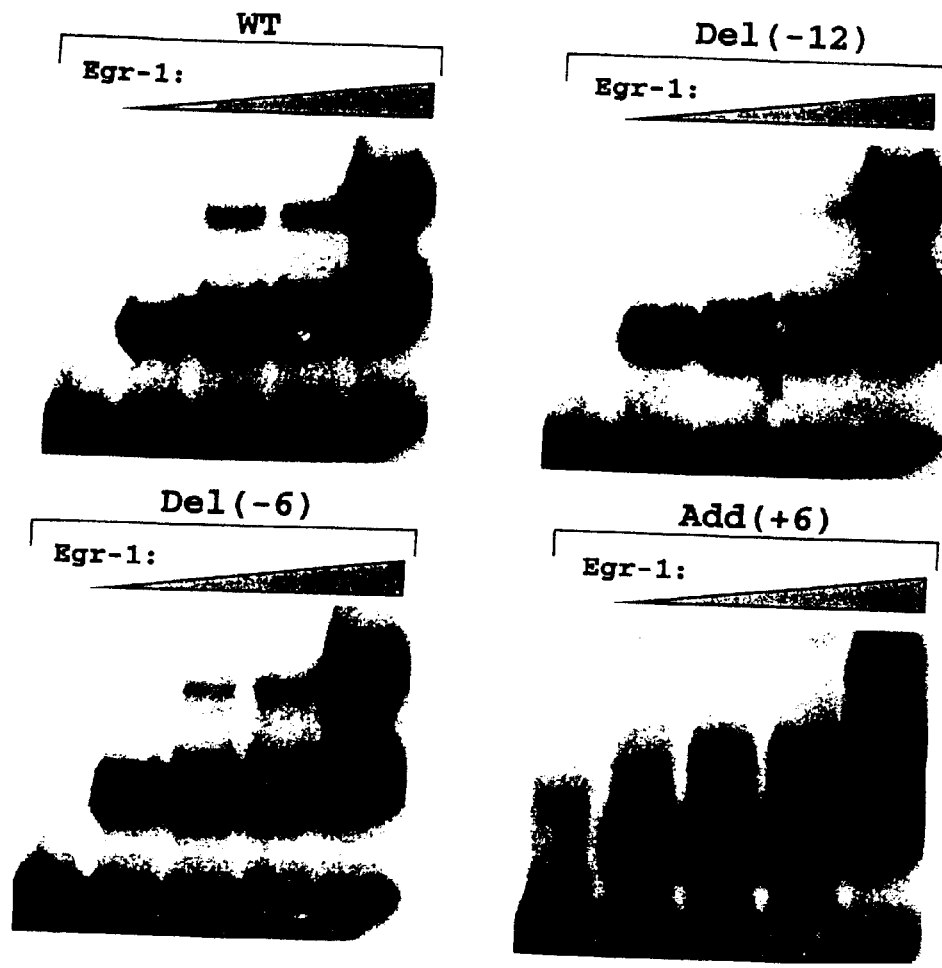
FIG. 8 shows EMSA using recombinant Egr-1 (zinc finger region) in increasing concentrations (0, 1:500, 1:200, 1:50, and 1:10).

EMSA's with the three mutant G+C-rich regions demonstrated that they are also capable of binding Sp1 and inducible Egr-1 (FIG. 7B). There are differences in the intensity and location of the Sp1 and Egr-1 bands among the different mutant DNAs. Sp1 and Egr-1 from nuclear extracts bound the wild type sequence with greater intensity than the mutant sequence; the relative intensity for mutants for Sp1 was 47 to 54% of the wild type while the relative intensity for Egr-1 was 42 to 67% of the wild type. Recombinant Egr-1 (FIG. 8) and Sp1 (data not shown) are both capable of binding all four oligonucleotides. Increasing concentrations of Egr-1 in proportion to radiolabeled oligonucleotide produced multiple bands with differences in the pattern of binding between will type and mutant oligonucleotides. The mutant consisting of a 6-bp addition produced three bands of greatest intensity, whereas the wild type and other mutants produced only two bands of lesser intensity. The wild type and 6-bp deletion of oligonucleotides bound slightly more intensely than the 12-bp deletion oligonucleotide. Recombinant Sp1 produced only one intense band, and there were no obvious differences in binding intensity between the different oligonucleotides.

EXAMPLE 2

Correlation of 5-Lipoxygenase Regulatory Polymorphisms with Responsiveness to Treatment with a 5-Lipoxygenase Inhibitor Patients with mild-to-moderate asthma who participated in one of two large clinical trails on the effectiveness of ZYFLO™ zileuton as asthma treatment (Israel et al., *JAMA* 275:931, 1996, incorporated herein by reference) were contacted by letter and asked to provide genetic material for analysis. Approximately 400 patients were contacted, 200 of whom had demonstrated a marked salutory response to ZYFLO™ zileuton and 200 of whom had not demonstrated such a response. Patients were asked to provide a buccal brush so that samples including genetic material would be obtained for analysis. Specifically, patients were given instructions to rinse their mouths out with water, to vigorously rub and rotate one brush on the inside surface of their right cheek for 30 second, and then to repeat the procedure with a second brush on their left cheek. Brushes were returned to us by mail. Response were received from 109 individuals and genotyping was successful for 88 of them.

For example sample, we detected the number of Sp1 binding motifs in the 5-lipoxygenase transcription factor binding region. Since the wild-type 5-lipoxygenase allele has 5 Sp1 motifs, individual homozygous for wild-type 5-lipoxygenase were designated "55". Similarly, individuals with one wild-type allele and one allele containing only 4 Sp1 motifes were designated "54", etc. The results are presented below in Table III:

TABLE III

Genotype of ZYFLO ™ Zileuton Study Patients

| Genotype | Number of patients |
|---|---|
| 55 | 43 |
| 45 | 31 |
| 44 | 10 |
| 35 | 2 |
| 34 | 1 |
| 56 | 1 |

The genotype information summarized above was correlated with the percent change in forced expiratory volume in the first second ($FEV_1$), which was the primary outcome in the ZYFLO™ zileuton clinical trial. The data are presented below in Table IV.

TABLE IV

Correlation of Genotype with $FEV_1$

| Number | Res/Non | % Predicted $FEV_1$ @ baseline | % Change from baseline | Genotype |
|---|---|---|---|---|
| 1 | R | 69.0 | 18.6 | 34 |
| 2 | N | 63.7 | −1.5 | 35 |
| 3 | R | 36.5 | 31.3 | 35 |
| 4 | N | 76.1 | −34.7 | 44 |
| 5 | N | 42.2 | 3.8 | 44 |
| 6 | R | 45.2 | 5.6 | 44 |
| 7 | R | 59.5 | 24.7 | 44 |
| 8 | R | 49.7 | 26.7 | 44 |
| 9 | R | 57.0 | 31.0 | 44 |
| 10 | R | 61.3 | 34.4 | 44 |
| 11 | R | 43.5 | 34.5 | 44 |
| 12 | R | 65.6 | 34.5 | 44 |

TABLE IV-continued

Correlation of Genotype with FEV$_1$

| Number | Res/Non | % Predicted FEV$_1$ @ baseline | % Change from baseline | Genotype |
|---|---|---|---|---|
| 13 | R | 51.5 | 63.5 | 44 |
| 14 | N | 76.8 | −45.2 | 45 |
| 15 | N | 77.5 | −36.1 | 45 |
| 16 | N | 56.9 | −33.0 | 45 |
| 17 | N | 77.5 | −26.0 | 45 |
| 18 | N | 76.3 | −19.9 | 45 |
| 19 | N | 78.8 | −9.9 | 45 |
| 20 | N | 58.0 | −9.5 | 45 |
| 21 | N | 59.4 | −7.3 | 45 |
| 22 | N | 75.5 | −6.7 | 45 |
| 23 | N | 74.3 | −4.7 | 45 |
| 24 | N | 70.2 | −2.5 | 45 |
| 25 | N | 77.1 | −1.7 | 45 |
| 26 | R | 43.6 | 1.7 | 45 |
| 27 | N | 65.3 | 4.7 | 45 |
| 28 | N | 49.1 | 6.5 | 45 |
| 29 | R | 51.4 | 10.3 | 45 |
| 30 | R | 78.7 | 13.3 | 45 |
| 31 | R | 76.0 | 14.5 | 45 |
| 32 | R | 64.5 | 15.2 | 45 |
| 33 | R | 75.5 | 15.6 | 45 |
| 34 | R | 72.8 | 15.7 | 45 |
| 35 | R | 57.4 | 19.6 | 45 |
| 36 | R | 53.2 | 19.7 | 45 |
| 37 | R | 67.8 | 20.6 | 45 |
| 38 | R | 54.2 | 24.7 | 45 |
| 39 | R | 61.3 | 33.1 | 45 |
| 40 | R | 41.9 | 35.1 | 45 |
| 41 | R | 67.1 | 48.4 | 45 |
| 42 | R | 61.2 | 49.7 | 45 |
| 43 | R | 43.8 | 65.6 | 45 |
| 44 | R | 44.4 | 75.6 | 45 |
| 45 | N | 42.0 | −20.3 | 56 |
| AVE | | 61.1 | 12.0 | |
| SD | | 12.7 | 27.2 | |
| SE | | 1.9 | 4.1 | |
| T-test | 0.0449 | | | |
| 46 | N | 81.7 | −18.6 | 55 |
| 47 | N | 76.7 | −17.9 | 55 |
| 48 | N | 74.0 | −17.2 | 55 |
| 49 | N | 70.0 | −14.7 | 55 |
| 50 | N | 72.8 | −12.4 | 55 |
| 51 | N | 76.6 | −11.2 | 55 |
| 52 | N | 67.4 | −10.8 | 55 |
| 53 | N | 78.8 | −9.2 | 55 |
| 54 | N | 71.2 | −6.1 | 55 |
| 55 | N | 76.4 | −5.4 | 55 |
| 56 | N | 67.7 | −4.0 | 55 |
| 57 | N | 78.5 | 0.3 | 55 |
| 58 | N | 71.2 | 0.3 | 55 |
| 59 | N | 49.8 | 1.0 | 55 |
| 60 | N | 67.4 | 1.7 | 55 |
| 61 | N | 50.2 | 3.4 | 55 |
| 62 | N | 62.8 | 5.3 | 55 |
| 63 | N | 67.7 | 6.4 | 55 |
| 64 | R | 47.3 | 8.4 | 55 |
| 65 | R | 41.9 | 12.5 | 55 |
| 66 | R | 54.9 | 14.6 | 55 |
| 67 | R | 71.1 | 25.4 | 55 |
| 68 | R | 67.5 | 25.6 | 55 |
| 69 | R | 65.6 | 29.8 | 55 |
| 70 | R | 65.5 | 30.1 | 55 |
| 71 | R | 65.3 | 31.1 | 55 |
| 72 | R | 54.1 | 32.7 | 55 |
| 73 | R | 66.3 | 34.1 | 55 |
| 74 | R | 61.5 | 35.4 | 55 |
| 75 | R | 61.3 | 36.2 | 55 |
| 76 | R | 36.5 | 36.5 | 55 |
| 77 | R | 67.7 | 37.0 | 55 |
| 78 | R | 44.2 | 38.4 | 55 |
| 79 | R | 45.0 | 40.1 | 55 |
| 80 | R | 42.2 | 44.7 | 55 |
| 81 | R | 43.2 | 49.6 | 55 |
| 82 | R | 53.9 | 56.6 | 55 |
| 83 | R | 61.3 | 57.7 | 55 |
| 84 | R | 52.6 | 62.5 | 55 |
| 85 | R | 55.4 | 64.2 | 55 |
| 86 | R | 42.1 | 87.1 | 55 |
| 87 | R | 36.6 | 91.3 | 55 |
| 88 | R | 42.0 | 97.9 | 55 |
| AVE | | 60.6 | 22.6 | |
| SD | | 12.9 | 30.7 | |
| SE | | 2.0 | 4.6 | |

As can be seen, the FEV$_1$ outcome was significantly (P=0.0449) greater in individuals harboring the wild-type genotype (55) than it was in the individuals harboring mutant genotypes. Specifically, individuals having the wild-type genotypes showed an average 22.6% increase in FEV$_1$ upon ZYFLO™ zileuton administration, whereas those with mutant genotypes showed an average 12% increase. These data suggest that individuals with mutant 5-lipoxygenase regulatory genotypes have reduced 5-lipoxygenase expression and therefore are benefitted less from pharmacologic down-regulation of the enzyme.

EXAMPLE 3

Large Scale Study to Identify Correlation Between 5-Lipoxygenase Regulatory Genotype with Response to Treatment with 5-Lipoxygenase Inhibitor Over 500 patients were enrolled in a prospective study analyzing the response of their asthma to treatment with zileuton in a controlled-release formulation (ZYFLO™ zileuton). Each of these patients will be genotyped at the 5-LO gene, and the clinical results will be stratified by genotype.

Other Embodiments

One of ordinary skill in the art will readily recognize that the foregoing has been merely a detailed description of certain preferred embodiments of the present invention. Various alterations and modifications of the procedures, techniques, and compositions described above will be apparent to those in the art and are intended to be encompassed by the following claims.

What is claimed is:

1. A method of identifying an asthma patient who is a candidate for effective treatment with 5-lipoxygenase inhibitors, the method comprising steps of:
   identifying a normal control individual who does not have asthma; and
   detecting an alteration in a 5-lipoxygenase gene regulatory sequence of the asthma patient as compared with the normal control individual, the presence of the alternation compared with the normal control individual identifying the patient as a candidate for effective treatment with 5-lipoxygenase inhibitors.

2. The method of claim 1 wherein the step of detecting an alteration comprises detecting an addition of a positive gene regulatory sequence in the 5-lipoxygenase gene regulatory sequence of the asthma patient as compared with the normal control individual.

3. The method of claim 1 wherein the step of detecting an alteration comprises detecting a disruption in a negative gene regulatory sequence in the 5-lipoxygenase gene regulatory sequence of the asthma patient as compared with the normal control individual.

4. A method of identifying an asthma patient who is not a candidate for effective treatment with 5-lipoxygenase inhibitors, the method comprising steps of:
   identifying a normal control individual who has normal levels of 5-lipoxygenase gene expression; and
   detecting an absence of an alteration in a 5-lipoxygenase gene regulatory sequence of the asthma patient as compared with the normal control individual, the absence of the alteration compared with the normal control individual identifying the patient as a patient who is not a candidate for effective treatment with 5-lipoxygenase inhibitors.

5. The method of claim 4 wherein the step of detecting the absence of the alteration comprises detecting an absence of a disruption in a negative gene regulatory sequence in the 5-lipoxygenase gene regulatory sequence of the asthma patient as compared with the normal control individual.

6. A method of identifying an asthma patient who is not a candidate for effective treatment with 5-lipoxygenase inhibitors comprising steps of:
   identifying a normal control individual who has normal levels of 5-lipoxygenase gene expression; and
   detecting an addition of a negative gene regulatory sequence in the 5-lipoxygenase gene regulatory sequence of the asthma patient as compared with the normal control individual.

7. A method of identifying an individual who has an increased susceptibility to an inflammatory disorder, the method comprising steps of:
   providing a nucleic acid sample from an individual; and
   detecting in the nucleic acid sample a 5-lipoxygenase gene polymorphism that correlates with the inflammatory disorder with a P value less than or equal to 0.05, existence of the polymorphism being indicative of increased susceptibility to the inflammatory disorder.

8. The method of claim 7 wherein the inflammatory disorder is selected from the group consisting of asthma, ulcerative colitis, bronchitis, sinusitis, psoriasis, allergic, and non-allergic rhinitis, lupus, and rheumatoid arthritis.

9. A method of classifying an individual as suffering from asthmas, the method comprising steps of:
   providing a nucleic acid sample from an asthmatic individual; and
   detecting in the nucleic acid sample a 5-lipoxygenase gene polymorphism that correlate with asthma with a P value less than or equal to 0.05, existence of the polymorphism being indicative of asthma.

10. A method of identifying an asthma patient who is a candidate for effective treatment with 5-lipoxygenase inhibitors, the method comprising steps of:
    detecting in a nucleic acid sample from an asthma patient a sequence polymorphism within a 5-lipoxygenase gate regulatory sequence, the polymorphism being correlated with responsiveness to 5-lipoxygenase inhibitors; and
    classifying the asthma patient, in light of the detected polymorphism, as a candidate for effective treatment with 5-lipoxygenase inhibitors.

11. A method of identifying an asthma patient who is not a candidate for effective treatment with 5-lipoxygenase inhibitors, the method comprising steps of:

detecting in a nucleic acid sample from an asthma patient a sequence polymorphism within a 5-lipoxygenase gene regulatory sequence, the polymorphism being correlated with lack of responsiveness to 5-lipoxygenase inhibitors; and classifying the asthma patient, in light of the detected polymorphism, as not a candidate for effective treatment with 5-lipoxygenase inhibitors.

* * * * *

SEQUENCE LISTING (1) GENERAL INFORMATION:

(iii) NUMBER OF SEQUENCES: 43

(2) INFORMATION FOR SEQ ID NO:1:

(i) SEQUENCE CHARACTERISTICS:
      (A) LENGTH: 2189 base pairs
      (B) TYPE: nucleic acid
      (C) STRANDEDNESS: both
      (D) TOPOLOGY: not relevant (ii) MOLECULE TYPE: DNA (genomic)

(vii) IMMEDIATE SOURCE:
      (B) CLONE: human 5-lipoxygenase gene (GenBank M 38191)

(xi) SEQUENCE DESCRIPTION: SEQ ID NO:1:

```
GGATCCAGAA TAACCAAAAC AATATTGAAA AATAAAGAAC AGCGTTGGTG GATTAACATT        60
TTCCAATTTC AAAACTTACT ATAGCACTGC GGTAATCAAG CAGTGTGGCA CTGTATAGCA       120
TGTACATTAC AGATCAGTGG ACTAGAATCA ATGTCCAGAA ATAAACCGTT ATGTTTATAA       180
TGAATTACTT TTTAATAAGG TGTCAAGACA ACGCAATGGG AAAAGAATAA TGAATTCAAC       240
AAATGATGCA TGGACAACCG GACATGCACA TGCAACACAA TGAATTTGAA TTCTTCTATC       300
GCTCCATGCA TAAAAACTAA CTCAAAATGG GTCACGGATG TAAATGAAAA GCTAAAACTA       360
TAATAATCCT AGAGGAAAAC CTAGGAGTAA ATCTTTAAGA TGTTATTGTA GGCAGTGGTT       420
TCTCAGATAG GACCCCAAAA TCACAAGCGA CAAAAAGAAA TTGGACTTAA AGTTAAATAC       480
TTTTGTGCTT CAAACATCAT CAAGAAAGTG AAAACACAAC CCGCAGAAGC AATAAAAATG       540
TCTGTAAGTC ATGTATCCGA TTAGAGACTT CTATCCAGGA TATATAAATA ATGCAATTCA       600
ATGATAAAAA AGATAAATAG CCCAGTTTTC CAAAGAGTCA AGCATCTGAA TATACATCTC       660
TCCAAAAATA TACAGATATC CAACAAGCAT GTGAAAAGAT GTTCAAAGCC ATTTGCCAGG       720
TGCACAAACC CAAGACAGTA TGAGGAGATG CTACAGGGAC TCTGCTGCTT CACAGACATG       780
AAGCGTTGGT GAGAATGTAG GCAGCCGCCT TTGGGGACTT CACATCCCCG CCGCCCCACG       840
CACGGTGAGC TAGTGTTTAA ACTTAGCCGA GATCAATACA CGCGACTGTG TGCCCGTCAG       900
ACCCTGCGCT GCCGGCGGGG CTGGGAGAGG CGGGCGCCAG GAGTGGGCGG GAACCTGGGG       960
GTCAGGCCCC AGCCGCGGGA AGCGCGCCCA GGAGCGCGCG AAACCTTCTC CACACCCTTC      1020
CAGGCATTTG CCCGCCGCGA TTCAGAGAGC CGACCCGTGA CCCCTGGCCT CCCCTAGACA      1080
GCCCCGCATG TCCAGATGTG CCGTCCCGCC TGCCTCCCGC GACCACTGGC CATCTCTGGG      1140
CCTGGGCGCG GTTCTCGGCG CCCGGCCTGC CCCCGCCAGG AGCCGCAGGT CCAGCCAGTG      1200
AAGAAGCCCG CGCCTGAAGG AGCCTCTGTG CTCCAGAATC CATCCTCAGT ATCAGCGCTG      1260
GGGTGGCCTC CTCCAGGAAG CCCTTCTGAT TCTCTCATGG GTCGCTCTTC CTCTGCAGAC      1320
TCCCGGAGCA CCCCCTGCTC CAAGTACCGC AAGTGGCACT GAGAACTTGG GGAGAGCAGA      1380
GGCTGTGCCT AGATTTGTAG GGAGTCCCCG CAGCTCCACC CCAGGGCCTA CAGGAGCCTG      1440
GCCTTGGGCG AAGCCGAGGC AGGCAGGCAG GGCAAAGGGT GGAAGCAATT CAGGAGAGAA      1500
CGAGTGAACG AATGGATGAG GGGTGGCAGC CGAGGTTGCC CCAGTCCCCT GGCTGCAGGA      1560
ACAGACACCT CGCTGAGGAG AGACCCAGGA GCGAGGCCCC TGCCCCGCCC GAGGCGAGGT      1620
CCCGCCCAGT CGGCGCCGCG CGTGAAGAGT GGGAGAGAAG TACTGCGGGG GCGGGGCGG       1680
```

```
GGGCGGGGGC GGGGGCGGGG GCAGCCGGGA GCCTGGAGCC AGACCGGGGC GGGGCCGGGA    1740

CCGGGGCCAG GGACCAGTGG TGGGAGGAGG CTGCGGCGCT AGATGCGGAC ACCTGGACCG    1800

CCGCGCCGAG GCTCCCGGCG CTCGCTGCTC CCGCGGCCCG CGCCATGCCC TCCTACACGG    1860

TCACCGTGGC CACTGGCAGC CAGTGGTTCG CCGGCACTGA CGACTACATC TACCTCAGCC    1920

TCGTGGGCTC GGCGGGCTGC AGCGAGAAGC ACCTGCTGGA CAAGCCCTTC TACAACGACT    1980

TCGAGCGTGG CGCGGTGAGC GCGGGCGGGG CACGGGTGGA GCGCGGGCTG AGGTGCGTCC    2040

GGGACCCGGT TTGGACGGCA GAGGCCTGGG CGGGGGCGCC GAGGGCCCGT CGGGGCGGCC    2100

CGGACAGGAC TGGGGGTGTC CAGGACCCTG TCAGGGAGGG CAGAACTGCG GTGGGGCGTG    2160

CCCTGGGCTC CCAGTGGCCG GTGGGTACC                                     2189
```

(2) INFORMATION FOR SEQ ID NO:2:

(i) SEQUENCE CHARACTERISTICS:
        (A) LENGTH: 28 base pairs
        (B) TYPE: nucleic acid
        (C) STRANDEDNESS: both
        (D) TOPOLOGY: not relevant (ii) MOLECULE TYPE: DNA (genomic)

(vii) IMMEDIATE SOURCE:
        (B) CLONE: 12 base pair deletion (xi) SEQUENCE DESCRIPTION: SEQ ID NO:2:

```
CGACGGGGGC GGGGGCGGGG GCGGGGGC                                        28
```

(2) INFORMATION FOR SEQ ID NO:3:

(i) SEQUENCE CHARACTERISTICS:
        (A) LENGTH: 12 base pairs
        (B) TYPE: nucleic acid
        (C) STRANDEDNESS: both
        (D) TOPOLOGY: not relevant (ii) MOLECULE TYPE: DNA (genomic)

(vii) IMMEDIATE SOURCE:
        (B) CLONE: 12 bp deleted (xi) SEQUENCE DESCRIPTION: SEQ ID NO:3:

```
GGCGGGGGCG GG                                                         12
```

(2) INFORMATION FOR SEQ ID NO:4:

(i) SEQUENCE CHARACTERISTICS:
        (A) LENGTH: 56 base pairs
        (B) TYPE: nucleic acid
        (C) STRANDEDNESS: both
        (D) TOPOLOGY: not relevant (ii) MOLECULE TYPE: DNA (genomic)

(vii) IMMEDIATE SOURCE:
        (B) CLONE: Normal tandem SP1 binding motifs in 5-LO (xi) SEQUENCE DESCRIPTION: SEQ ID NO:4:

```
GAGAAGTACT GCGGGGCGG GGGCGGGGC GGGGCGGGG GCGGGGCAG CCGGAC             56
```

(2) INFORMATION FOR SEQ ID NO:5:

(i) SEQUENCE CHARACTERISTICS:
        (A) LENGTH: 44 base pairs
        (B) TYPE: nucleic acid
        (C) STRANDEDNESS: both (D) TOPOLOGY: not relevant (ii) MOLECULE TYPE: DNA (genomic)

(vii) IMMEDIATE SOURCE:
        (B) CLONE: Normal tandem SP1 binding motif with 12 base pair
            deletion (xi) SEQUENCE DESCRIPTION: SEQ ID NO:5:

GAGAAGTACT GCGGGGCGG GGGCGGGGGC GGGGGCAGCC GGAC                44

(2) INFORMATION FOR SEQ ID NO:6:

(i) SEQUENCE CHARACTERISTICS:
        (A) LENGTH: 50 base pairs
        (B) TYPE: nucleic acid
        (C) STRANDEDNESS: both
        (D) TOPOLOGY: not relevant (ii) MOLECULE TYPE: DNA (genomic)

(vii) IMMEDIATE SOURCE:
        (B) CLONE: Normal tandem SP1 binding motif with 6 base pair
            deletion (xi) SEQUENCE DESCRIPTION: SEQ ID NO:6:

GAGAAGTACT GCGGGGCGG GGGCGGGGGC GGGGGCGGGG GCAGCCGGAC            50

(2) INFORMATION FOR SEQ ID NO:7:

(i) SEQUENCE CHARACTERISTICS:
        (A) LENGTH: 56 base pairs
        (B) TYPE: nucleic acid
        (C) STRANDEDNESS: both
        (D) TOPOLOGY: not relevant (ii) MOLECULE TYPE: DNA (genomic)

(vii) IMMEDIATE SOURCE:
        (B) CLONE: Normal tandem SP1 binding motif with 6 base pair
            addition (xi) SEQUENCE DESCRIPTION: SEQ ID NO:7:

TNCTNCCGGG GCGGGGCGG GGGCGGGGGC GGGGGCGGGG GCGGGGGCAG CCGGAC       56

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(vii) IMMEDIATE SOURCE:
        (B) CLONE: Negative regulatory region sense primer (xi) SEQUENCE DESCRIPTION: SEQ ID NO:8:

AAAGAACAGC GTTGGTGGAT                                           20

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "primer"

(vii) IMMEDIATE SOURCE:
        (B) CLONE: Negative regulatory region antisense primer (xi) SEQUENCE DESCRIPTION: SEQ ID NO:9:

CAAATTCATT GTGTTGCATG TG                                              22

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(vii) IMMEDIATE SOURCE:
        (B) CLONE: -292 to -727 sense primer (xi) SEQUENCE DESCRIPTION: SEQ ID NO:10:

ACCACTGGCC ATCTCTGG                                                   18

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(vii) IMMEDIATE SOURCE:
        (B) CLONE: -292 to -727 antisense primer (xi) SEQUENCE DESCRIPTION: SEQ ID NO:11:

CTCTCAGCGA GGTGTCTG                                                   18

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(vii) IMMEDIATE SOURCE:
        (B) CLONE: Positive regulatory region sense primer (xi) SEQUENCE DESCRIPTION: SEQ ID NO:12:

TTAGCCGAGA TCAATACACG C                                               21

(2) INFORMATION FOR SEQ ID NO:13:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(vii) IMMEDIATE SOURCE:

(B) CLONE: Positive regulatory region antisense primer (xi) SEQUENCE DESCRIPTION: SEQ ID NO:13:

GGGTGTGGAG AAGGTTTCG                                                    19

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(vii) IMMEDIATE SOURCE:
        (B) CLONE: Transcription factor binding region sense primer (xi) SEQUENCE DESCRIPTION: SEQ ID NO:14:

AGGAACAGAC ACCTCCTGAG GAGCA                                             25

(2) INFORMATION FOR SEQ ID NO:15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(vii) IMMEDIATE SOURCE:
        (B) CLONE: Transcription factor binding region antisense
            primer (xi) SEQUENCE DESCRIPTION: SEQ ID NO:15:

GAGCAGCGAG CGGGAGCCTC GGC                                               23

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(vii) IMMEDIATE SOURCE:
        (B) CLONE: Exon 1 sense primer (xi) SEQUENCE DESCRIPTION: SEQ ID NO:16:

CGCCATGCCC TCCTACAC                                                     18

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(vii) IMMEDIATE SOURCE:
        (B) CLONE: Exon 1 antisense primer (xi) SEQUENCE DESCRIPTION: SEQ ID NO:17:

CCACGCTGGA AGTCGTTGTA                                                    20

(2) INFORMATION FOR SEQ ID NO:18:

(i) SEQUENCE CHARACTERISTICS:
           (A) LENGTH: 18 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "primer"

(vii) IMMEDIATE SOURCE:
           (B) CLONE: Exon 2 sense primer (xi) SEQUENCE DESCRIPTION: SEQ ID NO:18:

TCTCCTTCCC AGGTGGAT                                                      18

(2) INFORMATION FOR SEQ ID NO:19:

(i) SEQUENCE CHARACTERISTICS:
           (A) LENGTH: 13 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "primer"

(vii) IMMEDIATE SOURCE:
           (B) CLONE: Exon 2 antisense primer (xi) SEQUENCE DESCRIPTION: SEQ ID NO:19:

GCTCACCGCG TCC                                                           13

(2) INFORMATION FOR SEQ ID NO:20:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "primer"

(vii) IMMEDIATE SOURCE:
           (B) CLONE: Exon 3 sense primer (xi) SEQUENCE DESCRIPTION: SEQ ID NO:20:

CTTTCTTTAC AGCAAAGTTG                                                    20

(2) INFORMATION FOR SEQ ID NO:21:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "primer"

(vii) IMMEDIATE SOURCE:
           (B) CLONE: Exon 3 antisense primer (xi) SEQUENCE DESCRIPTION: SEQ ID NO:21:

TACACACTCA CCGATATTG                                                     19

(2) INFORMATION FOR SEQ ID NO:22:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(vii) IMMEDIATE SOURCE:
        (B) CLONE: Exon 4 sense primer (xi) SEQUENCE DESCRIPTION: SEQ ID NO:22:

TCTCATGCTC AGATGGATG                                              19

(2) INFORMATION FOR SEQ ID NO:23:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(vii) IMMEDIATE SOURCE:
        (B) CLONE: Exon 4 antisense primer (xi) SEQUENCE DESCRIPTION: SEQ ID NO:23:

ACTTACGCTT TGGA                                                   14

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(vii) IMMEDIATE SOURCE:
        (B) CLONE: Exon 5 sense primer (xi) SEQUENCE DESCRIPTION: SEQ ID NO:24:

TGGAGAACCT GTTCATCAAC C                                           21

(2) INFORMATION FOR SEQ ID NO:25:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(vii) IMMEDIATE SOURCE:
        (B) CLONE: Exon 5 antisense primer (xi) SEQUENCE DESCRIPTION: SEQ ID NO:25:

TCACCAGAAA TAGTGTTGCT GA                                          22

(2) INFORMATION FOR SEQ ID NO:26:

```
        (i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(vii) IMMEDIATE SOURCE:
            (B) CLONE: Exon 6 sense primer (xi) SEQUENCE DESCRIPTION: SEQ ID NO:26:

CCTGGTAGAG CGGGTCATGA ATC                                              23

(2) INFORMATION FOR SEQ ID NO:27:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(vii) IMMEDIATE SOURCE:
            (B) CLONE: Exon 6 antisense primer (xi) SEQUENCE DESCRIPTION: SEQ ID NO:27:

ACCTCCTGCT CCAAGCTGAG CT                                               22

(2) INFORMATION FOR SEQ ID NO:28:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(vii) IMMEDIATE SOURCE:
            (B) CLONE: Exon 7 sense primer (xi) SEQUENCE DESCRIPTION: SEQ ID NO:28:

TCGCTCCTGC AGCAAGGG                                                    18

(2) INFORMATION FOR SEQ ID NO:29:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(vii) IMMEDIATE SOURCE:
            (B) CLONE: Exon 7 antisense primer (xi) SEQUENCE DESCRIPTION: SEQ ID NO:29:

GCCTACCTGG AT                                                          12

(2) INFORMATION FOR SEQ ID NO:30:

(i) SEQUENCE CHARACTERISTICS:
            (A) LENGTH: 18 base pairs
```

```
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(vii) IMMEDIATE SOURCE:
            (B) CLONE: Exon 8 sense primer (xi) SEQUENCE DESCRIPTION: SEQ ID NO:30:

CCAATGTATG AGCTCAAC                                                   18

(2) INFORMATION FOR SEQ ID NO:31:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(vii) IMMEDIATE SOURCE:
            (B) CLONE: Exon 8 antisence primer (xi) SEQUENCE DESCRIPTION: SEQ ID NO:31:

GCTATCCTGT ACCTTGAA                                                   18

(2) INFORMATION FOR SEQ ID NO:32:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(vii) IMMEDIATE SOURCE:
            (B) CLONE: Exon 9 sense primer (xi) SEQUENCE DESCRIPTION: SEQ ID NO:32:

CCCTCCCCAG CTGCTGGT                                                   18

(2) INFORMATION FOR SEQ ID NO:33:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(vii) IMMEDIATE SOURCE:
            (B) CLONE: Exon 9 antisense primer (xi) SEQUENCE DESCRIPTION: SEQ ID NO:33:

ACCCACCTTG TCAAAGCGGC C                                               21

(2) INFORMATION FOR SEQ ID NO:34:

(i) SEQUENCE CHARACTERISTICS:
            (A) LENGTH: 20 base pairs
            (B) TYPE: nucleic acid
            (C) STRANDEDNESS: single
            (D) TOPOLOGY: linear
```

(ii) MOLECULE TYPE: other nucleic acid
    (A) DESCRIPTION: /desc = "primer"

(vii) IMMEDIATE SOURCE:
    (B) CLONE: Exon 10 sense primer (xi) SEQUENCE DESCRIPTION: SEQ ID NO:34:

CACTCCAGGC CAACGCCACA                                         20

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(vii) IMMEDIATE SOURCE:
        (B) CLONE: Exon 10 antisense primer (xi) SEQUENCE DESCRIPTION: SEQ ID NO:35:

CCACACCAGG AGCCCGTCGT                                         20

(2) INFORMATION FOR SEQ ID NO:36:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(vii) IMMEDIATE SOURCE:
        (B) CLONE: Exon 11 sense primer (xi) SEQUENCE DESCRIPTION: SEQ ID NO:36:

CCCCTGAGCC AGGTTCACG                                          19

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(vii) IMMEDIATE SOURCE:
        (B) CLONE: Exon 11 antisense primer (xi) SEQUENCE DESCRIPTION: SEQ ID NO:37:

CCACGAACCC TACCTGAGGA                                         20

(2) INFORMATION FOR SEQ ID NO:38:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

```
      (vii) IMMEDIATE SOURCE:
            (B) CLONE: Exon 12 sense primer (xi) SEQUENCE DESCRIPTION: SEQ ID NO:38:

TTCCACCCTA GGCTTCCC                                                18

(2) INFORMATION FOR SEQ ID NO:39:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(vii) IMMEDIATE SOURCE:
            (B) CLONE: Exon 12 antisense primer (xi) SEQUENCE DESCRIPTION: SEQ ID NO:39:

GCCTACCTGG CCGAAGTT                                                18

(2) INFORMATION FOR SEQ ID NO:40:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(vii) IMMEDIATE SOURCE:
            (B) CLONE: Exon 13 sense primer (xi) SEQUENCE DESCRIPTION: SEQ ID NO:40:

GTGCTCCTGG ATCCCCAAT                                               19

(2) INFORMATION FOR SEQ ID NO:41:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(vii) IMMEDIATE SOURCE:
            (B) CLONE: Exon 13 antisense primer (xi) SEQUENCE DESCRIPTION: SEQ ID NO:41:

CTCGTTTTCC TGGAACTGGC                                              20

(2) INFORMATION FOR SEQ ID NO:42:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(vii) IMMEDIATE SOURCE:
            (B) CLONE: Exon 14 sense primer
```

```
       (xi) SEQUENCE DESCRIPTION: SEQ ID NO:42:

CTGGGCCCTC AGCTGTTC                                                    18

(2) INFORMATION FOR SEQ ID NO:43:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "primer"

(vii) IMMEDIATE SOURCE:
           (B) CLONE: Exon 14 antisense primer (xi) SEQUENCE DESCRIPTION: SEQ ID NO:43:

CACATGGAAC AAGACCCATT                                                  20
```